(12) United States Patent  
Voss et al.

(10) Patent No.: US 8,440,855 B2  
(45) Date of Patent: May 14, 2013

(54) PROCESS FOR THE PRODUCTION OF ACETIC ACID ETHYLENE AND VINYL ACETATE MONOMER

(75) Inventors: Bodil Voss, Virum (DK); Rachid Mabrouk, Malmö (SE); Claus Hviid Christensen, Lynge (DK)

(73) Assignee: Haldor Topsoe A/S, Lyngby (DK)

( * ) Notice: Subject to any disclaimer, the term of this patent is extended or adjusted under 35 U.S.C. 154(b) by 261 days.

(21) Appl. No.: 12/963,402

(22) Filed: Dec. 8, 2010

(65) Prior Publication Data

US 2011/0137074 A1 Jun. 9, 2011

(30) Foreign Application Priority Data

Dec. 8, 2009 (DK) .................................. 2009 01291

(51) Int. Cl.  
*C07C 67/04* (2006.01)

(52) U.S. Cl.  
USPC ......................................................... 560/247

(58) Field of Classification Search ........................ None  
See application file for complete search history.

(56) References Cited

U.S. PATENT DOCUMENTS

| 4,670,620 A * | 6/1987 | Jacobs et al. ................... 585/640 |
| 6,022,823 A | 2/2000 | Augustine et al. |
| 6,057,260 A | 5/2000 | Nicolau et al. |
| 6,472,556 B2 | 10/2002 | Kitchen et al. |
| 2005/0209483 A1 * | 9/2005 | Bhaskaran et al. ............ 560/241 |
| 2006/0116528 A1 | 6/2006 | Mazanec et al. |
| 2008/0234511 A1 * | 9/2008 | Michl ............................ 560/231 |

FOREIGN PATENT DOCUMENTS

| WO | WO 2005/092829 A1 | 10/2005 |
| WO | WO 2008/110468 A1 | 9/2008 |

* cited by examiner

*Primary Examiner* — Karl J Puttlitz  
(74) *Attorney, Agent, or Firm* — Dickstein Shapiro LLP

(57) ABSTRACT

An integrated process for the production of acetic acid, ethylene and vinyl acetate monomer comprising the steps of:

(a) evaporating at least part of an ethanol feed stock  
(b) producing in a first reaction zone a first product stream comprising acetic acid by oxidative or partly oxidative dehydrogenation of ethanol feed stock;  
(c) producing in a second reaction zone a second product stream comprising ethylene from an ethanol feed stock;  
(d) reacting in a third reaction zone an acetic acid reaction stream containing at least a portion of the acetic acid from the first reaction zone with an ethylene reaction stream containing at least a portion of the ethylene product from the second reaction zone and with oxygen to a third product stream comprising vinyl acetate monomer;  
(e) passing at least a portion of the third product stream to a distillation section and isolating at least a portion of the vinyl acetate monomer;  
(f) supplying at least part of reaction heat from the third reaction zone to provide heat for evaporating at least part of the ethanol feed stock in step (a);  
(g) supplying at least part of reaction heat from the first reaction zone to provide heat for producing the second product stream in the second reaction zone in step (c) and for distilling of the third product stream in the distillation section in step (e).

10 Claims, 1 Drawing Sheet

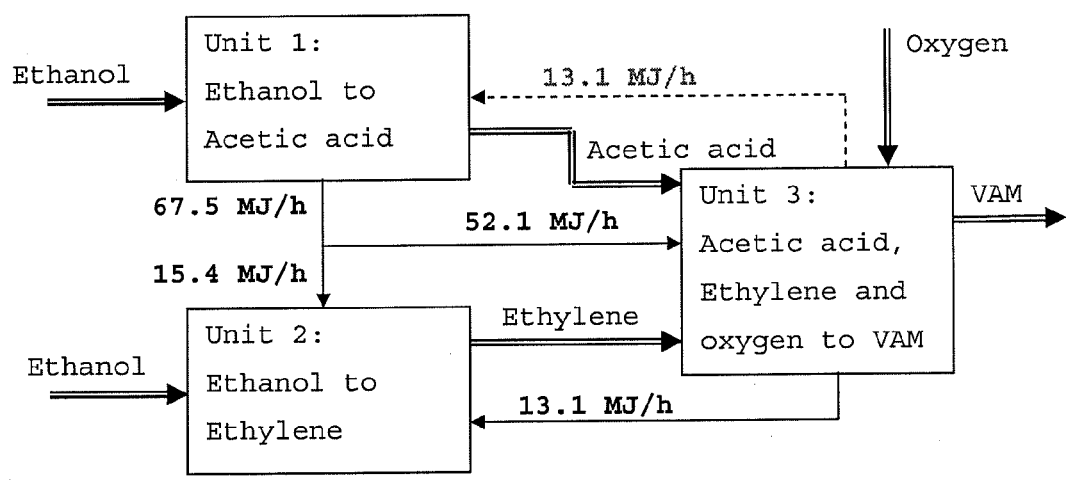

PROCESS FOR THE PRODUCTION OF ACETIC ACID ETHYLENE AND VINYL ACETATE MONOMER

This invention relates to an improved process for the preparation of ethylene and acetic acid being and use of these compounds as feed stock in the production of vinyl acetate monomer (VAM). In particular, the invention is directed to internal supply of heat to the VAM process by an integrated process comprising heat transfer between all steps of the process.

Since the 1960's processes were developed for the production of VAM from ethylene, oxygen and acetic acid in presence of catalysts comprising Pd optionally doped with Au, Rh or Cd and promoted with alkali acetate by the following reaction:

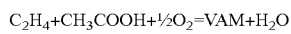

$$C_2H_4+CH_3COOH+\tfrac{1}{2}O_2=VAM+H_2O$$

This reaction is accompanied by the detrimental side reaction of complete ethylene oxidation:

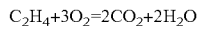

$$C_2H_4+3O_2=2CO_2+2H_2O$$

Due to the sensitivity of the catalyst, the temperature must be kept below a certain temperature depending on the actual catalyst.

In addition to the above catalysts, other catalysts being useful in the production of VAM are known in the art. Examples of such catalysts are mentioned in U.S. Pat. No. 6,022,823, U.S. Pat. No. 6,057,260 and U.S. Pat. No. 6,472,556. The catalysts may be supported on carriers including silica, silica-alumina or other metal oxides.

Typically, the upper temperature limit in the VAM synthesis is 200° C. and the lower temperature limit is 130° C. Below 130° C. the activity of the catalyst is insufficient and there exists a risk of condensation of acetic acid. This leaves a relatively small range of feasible operating temperatures for the VAM synthesis.

In addition to concerns about catalyst stability and activity, the selectivity for formation of the desired VAM product decreases with increasing temperature.

The VAM reaction proceeds exothermically with production of heat. Thus, in order to maintain a proper temperature profile in the reaction zone within the allowed temperature range, means for the management of the reaction heat must be provided through external or internal removal of heat. Different means for heat management are being applied in the industry or mentioned in connection with the production of VAM.

Conventionally, a tube and shell reactor with the catalyst contained inside the tubes and with boiling water on the outer shell side is applied. In such a reactor the heat of reaction is removed by generation of low pressure steam with a temperature being equal to the tube wall temperature. In order to prevent the temperature to rise above 200° C. inside the catalyst bed, the boiling water temperature is typically not higher than about 180-185° C., sometimes less than 160° C.

A drawback of the boiling water cooled reactor is that the temperature of the process generated steam varies over time. The deactivation of the VAM catalyst over time is compensated by increase of the operating temperature, which requires an increased boiling water temperature.

Alternatively, the catalytic conversion according to the above reaction may take place in a fluidised bed reactor based process, where a substantially constant temperature is obtained in the catalyst bed due to back-mixing of catalyst particles and reaction medium. The fluidised bed operation is a rather expensive process with high requirements to mechanical stability of the catalyst particles.

Another method of maintaining the operating temperature below 200° C. is staged addition of cooler oxygen or other reactants to the process, as mentioned in US 2006/0116528 A1.

The quench arrangement provides several advantages. By the staged oxygen addition, a higher conversion of ethylene per pass is possible, because more oxygen can be added observing the limitations on oxygen concentration (set to avoid the risk of explosion), the reduction of selectivity and thereby potential temperature run-away. Additionally, an improved temperature control is obtained by the direct cooling through addition of cool oxygen feed. Furthermore an improved activity may be obtained when keeping the average ethylene partial pressure higher. Cooling channels may be arranged adjacent to the channels containing the catalyst particles, further improving the temperature control and minimising the need for internal cooling through inert recycling.

As a main disadvantage, the quench reactor produces less steam than a boiling water reactor and it is a complex equipment.

Common to the known methods for the removal of reaction heat by steam generation in the VAM process is that the process-generated steam temperature is too low for the steam can used in the distillation section of the VAM unit downstream of the VAM reactor. The VAM distillation section needs a heating medium such as low/medium pressure steam at 160 to 250° C. in order to be operable. Typically steam is imported to the VAM facility in order to cover the VAM plant steam deficit. The steam condensate is returned/exported from the VAM distillation section.

An improved process-generated steam quality is obtained by compressing the process-generated steam as disclosed in US 2008/0234511 A1. Thereby the quality of the process generated steam and its pressure level is changed to provide saturated steam qualities at 160-200° C., often superheated up to 250° C. Steam compression is, however, an expensive method and the steam deficit for the distillation section is only halved.

Another method of heat supply to a VAM plant is to transfer heat required from a neighbouring acetic acid plant, either through heat exchange or via generated steam as heat transferring medium. WO 2005/092829 suggests transferring a portion of heat produced during the production of acetic acid to a VAM feed stream and/or to the VAM distillation section.

Despite of the above discussed efforts, a need remains to design a process for the preparation of VAM with a sufficient heat supply to the distillation section.

As mentioned above, the feed stock in the VAM process is acetic acid, ethylene and oxygen.

Oxygen is conventionally produced in oxygen plants involving low temperature distillation.

Ethylene may be produced by different methods. As an example, ethylene may be obtained through steam cracking of naphtha, through the conversion of methanol in the so-called MTO process with a mixture of ethylene and propylene as products, or it may be produced with high selectivity and yield in the ethanol dehydration reaction:

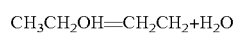

$$CH_3CH_2OH=CH_2CH_2+H_2O$$

The dehydration of ethanol to ethylene proceeds endothermic and is industrially carried out in a heated fixed bed catalytic reactor typically at a temperature in the range of 300-450° C.

Examples of catalysts being active in dehydrating of ethanol to ethylene include zeolites and supported or unsupported metal oxides such as $ZnO/Al_2O_3$, $FeO/Al_2O_3$, $Mn_2O_3/Al_2O_3$.

Water containing ethanol may be used as a feed stock for the dehydration of ethanol to ethylene.

Ethanol feed stock can be produced by fermentation of carbohydrate containing materials. In this process the ethanol product is obtained in an aqueous solution with an ethanol concentration of 5-15% by weight together with fermentation by-products and solids, the so-called broth.

Ethanol can be converted by dehydrogenation to acetic acid via the oxidative and/or the non-oxidative route, according to the following reaction schemes:

$$EtOH + O_2 => HOAc + H_2O \text{ (oxidative route, 180-320° C.)} \quad (1)$$

$$\Delta H^1 = 439 \text{ kJ/mole}$$

$$EtOH + H_2O = HOAc + 2H_2 \text{ (non-oxidative route, 250-350° C.)} \quad (2)$$

$$\Delta H^1 = -44 \text{ kJ/mole}$$

Whereas the oxidative route is exothermic and not limited by equilibrium, the non-oxidative route is endothermic and equilibrium limited and proceeds via intermediate acetaldehyde formation.

Copper or copper based materials are suitable catalysts for the non-oxidative dehydrogenation of ethanol to acetic acid. Other catalysts e.g. coal capable of converting ethanol at non-oxidative conditions to acetic acid, are mentioned as well in the literature.

Examples of catalysts active in the oxidative conversion of ethanol to acetic acid are vanadium oxide, nano-gold particles and supported palladium.

The conversion of ethanol to acetic acid may be carried out by a combination of the oxidative and the non-oxidative reaction.

It has now been found that the processes for the preparation of acetic acid, ethylene and the VAM process can advantageously be integrated or combined, so that the heat requirements of the VAM distillation section are met, while at the same time excess heat from the VAM process is used in the acetic acid and/or the ethylene processes.

Pursuant to this finding, this invention provides an integrated process for the production of acetic acid, ethylene and vinyl acetate monomer comprising the steps of:
(a) evaporating at least part of an ethanol feed stock
(b) producing in a first reaction zone a first product stream comprising acetic acid by oxidative or partly oxidative dehydrogenation of ethanol feed stock;
(c) producing in a second reaction zone a second product stream comprising ethylene from an ethanol feed stock;
(d) reacting in a third reaction zone an acetic acid reaction stream containing at least a portion of the acetic acid from the first reaction zone with an ethylene reaction stream containing at least a portion of the ethylene product from the second reaction zone and with oxygen to a third product stream comprising vinyl acetate monomer;
(e) passing at least a portion of the third product stream to a distillation section and isolating at least a portion of the vinyl acetate monomer;
(f) supplying at least part of reaction heat from the third reaction zone to provide heat for evaporating at least part of the ethanol feed stock in step (a);
(g) supplying at least part of reaction heat from the first reaction zone to provide heat for producing the second product stream in the second reaction zone in step (c) and for distilling of the third product stream in the distillation section in step (e).

By the term "partly oxidative dehydrogenation" as used hereinbefore and in the following is meant a combination of the above described oxidative and the non-oxidative route as shown by reaction (1) and (2)

An advantage of the invention is that the heat of reaction being formed during the VAM producing reaction is used in the evaporation of ethanol feed stock for the formation of ethylene and acetic acid and the heat of reaction from the ethylene and acetic acid reactions is at the same time used in the distillation of the VAM raw product, so that there will be no heat export to an external process unit.

A further advantage of the invention is that the ethanol feed stock in the step (a) and (b) may contain water.

The reaction heat being formed in the first reaction zone during the oxidative or partly oxidative dehydrogenation of ethanol is preferably transferred to the second reaction zone to supply heat for the endothermic dehydration of ethanol to ethylene and to the VAM distillation section. Simultaneously, the reaction heat being formed in the third reaction zone is preferably transferred to the first and/or the second reaction zone.

The supply of heat to the various reaction zones may proceed according to any known means of heat transfer. A preferred method in the inventive process is an indirect heat exchange between the media to supply/absorb heat or via a heating agent carrier. Typically the heating agent is steam, but other agents like thermo-stabile oils, like Dowtherm® may also be used.

In an embodiment of the invention, reaction heat from the VAM synthesis section is used to generate steam from boiler feed water in a boiling water cooled reactor and/or a boiler. The steam, a 160° C. saturated steam, may be flashed to a stream of superheated steam better suited as heating agent for the evaporation of ethanol in a heat exchanger (evaporator). The steam is transferred to the ethanol evaporator/s in the acetic acid and/or ethylene processes. The reaction heat from the acetic acid process is used to generate steam in a boiler and/or a boiling water cooled reactor at a higher temperature level, e.g. 320° C., a part of which is transferred to a steam heated ethylene reactor and the remainder is flashed to the appropriate temperature levels of the VAM distillation section, about 250° C. and 200° C., respectively.

Suitable catalysts for the various reactions in the process according to the invention are well known in the art as discussed hereinbefore.

In further an embodiment, the two ethanol feed stock streams may contain water, and optionally at different concentrations between 0-90 wt %, primarily balanced by ethanol. Minute amounts of by-products in the ethanol feed streams being tolerable under the concern of the synthesis in question and the VAM synthesis may be present as well.

In still an embodiment, only part of the acetic acid and ethylene production is used as feed streams for the VAM synthesis.

Further aspects and features of the invention will be illustrated in more detail in the following Examples

EXAMPLE

This is an example of the present invention which demonstrates the heat integration is made possible through the process integration of three process units with reference to FIG. 1 in the drawings.

Process stream lines are indicated by double lined arrows and heat transfer lines are indicated by single line arrows.

Two feed stream lines of pure ethanol are provided from an external ethanol source (not shown).

In unit 1 acetic acid is prepared by conversion of a first ethanol feed stream via the oxidative or at least partly oxidative reaction, resulting in at least 217 kJ/mole reaction heat or 67.5 MJ/h at a temperature of 320° C.

In unit 2 a second ethanol feed stream is dehydrated to ethylene at 300° C., wherein the reaction heat produced in unit 1 is transferred to unit 2. In unit 2 the heat provided from unit 1 serves both to the isothermal dehydration of ethanol (14.7 MJ/h) and to the feed preheating from e.g. 280° C. (0.6 MJ/h) to the reaction temperature, and losses (0.1 MJ/h).

In unit 3 vinyl acetate monomer (VAM) is produced by conversion of acetic acid, ethylene and oxygen with a selectivity to VAM of 99% from acetic acid and 94% from ethylene.

The heat exported from the VAM unit 3 is used as heat of evaporation of the ethanol feed stock (13.1 MJ/h) in unit 2. The amount of steam for heating the VAM distillation corresponds to an energy flow of 52.1 MJ/h transferred from the first unit as 320° C. hot saturated steam, being flashed to the preferred operating temperatures 200 and 250° C., respectively.

The example represents one embodiment of the invention. In another embodiment the heat exported from the VAM unit may be used as heat of evaporation in unit 1. This alternative is indicated with dotted lines in FIG. 1.

The invention claimed is:

1. An integrated process for the production of acetic acid, ethylene and vinyl acetate monomer comprising the steps of:
    (a) evaporating at least part of an ethanol feed stock to obtain an evaporated ethanol feed stock;
    (b) producing in a first reaction zone a first product stream comprising acetic acid by oxidative or partly oxidative dehydrogenation of ethanol feed stock or the evaporated ethanol feed stock from step (a);
    (c) producing in a second reaction zone a second product stream comprising ethylene from ethanol feed stock or the evaporated ethanol feed stock from step (a);
    (d) reacting in a third reaction zone an acetic acid reaction stream containing at least a portion of the acetic acid from the first reaction zone with an ethylene reaction stream containing at least a portion of the ethylene product from the second reaction zone and with oxygen to a third product stream comprising vinyl acetate monomer;
    (e) passing at least a portion of the third product stream to a distillation section and isolating at least a portion of the vinyl acetate monomer;
    (f) supplying at least part of reaction heat from the third reaction zone to provide heat for evaporating at least part of the ethanol feed stock in step (a); and
    (g) supplying at least part of reaction heat from the first reaction zone to provide heat for producing the second product stream in the second reaction zone in step (c) and for distilling of the third product stream in the distillation section in step (e).

2. The process of claim 1, wherein the ethanol feed stock being evaporated in step (a) is fed to the first reaction zone.

3. The process of claim 1, wherein the ethanol feed stock being evaporated in step (a) is fed to the second reaction zone.

4. The process of claim 1, wherein the at least part of the reaction heat being removed from the first reaction zone is supplied to the second reaction zone by means of steam via a steam system.

5. The process of claim 1, wherein the at least part of the reaction heat from the third reaction zone is supplied by means of steam via a steam system.

6. The process of claim 4, wherein high pressure steam condensate being formed by transferring heat in the steam system to the second reaction zone is flashed to create steam at a lower pressure, which is passed to the distillation section in step (e) for the supply of heat.

7. The process of claim 4, wherein high pressure steam condensate formed by the steam transferring heat to the second reaction zone is recycled to the first reaction zone to absorbing heat by forming high pressure steam.

8. The process of claim 1, wherein the ethanol feed stock contains water.

9. The process of claim 1, wherein the ethanol feed stock being used in steps (c) and (d) originates from a single ethanol source.

10. The process of claim 1, wherein the ethanol feed stock being used in steps (a) and (b) originates from one or more distillates of ethanol produced through the fermentation of carbohydrates.

* * * * *